United States Patent [19]

Sutcu et al.

[11] Patent Number: 5,549,604

[45] Date of Patent: Aug. 27, 1996

[54] NON-STICK ELECTROCONDUCTIVE AMORPHOUS SILICA COATING

[75] Inventors: Maz Sutcu, New Hartford; John S. Gentelia, Madison, both of N.Y.; Eray Aydil, Goleta, Calif.

[73] Assignee: Conmed Corporation, Utica, N.Y.

[21] Appl. No.: 254,072

[22] Filed: Dec. 6, 1994

[51] Int. Cl.⁶ .................................................... A61B 17/36
[52] U.S. Cl. ............................... 606/45; 606/39; 606/41
[58] Field of Search ........................... 606/27–29, 32–34, 606/37–42, 45–52; 607/100–102, 115, 116; 128/639–642

[56] References Cited

U.S. PATENT DOCUMENTS

| | | |
|---|---|---|
| 3,754,329 | 8/1973 | Lane . |
| 4,012,551 | 3/1977 | Bogaty et al. . |
| 4,161,950 | 7/1979 | Doss et al. . |
| 4,314,559 | 2/1982 | Allen . |
| 4,333,467 | 6/1982 | Domicone . |
| 4,481,057 | 11/1984 | Beard . |

*Primary Examiner*—Angela D. Sykes
*Assistant Examiner*—Michael Peffley
*Attorney, Agent, or Firm*—Larson and Taylor

[57] ABSTRACT

The cutting surfaces of electrosurgical instruments are provided with an electroconductive coating of an inorganic silicon-containing non-stick material such as amorphous silica deposited thereon by plasma enhanced chemical vapor deposition.

16 Claims, 1 Drawing Sheet

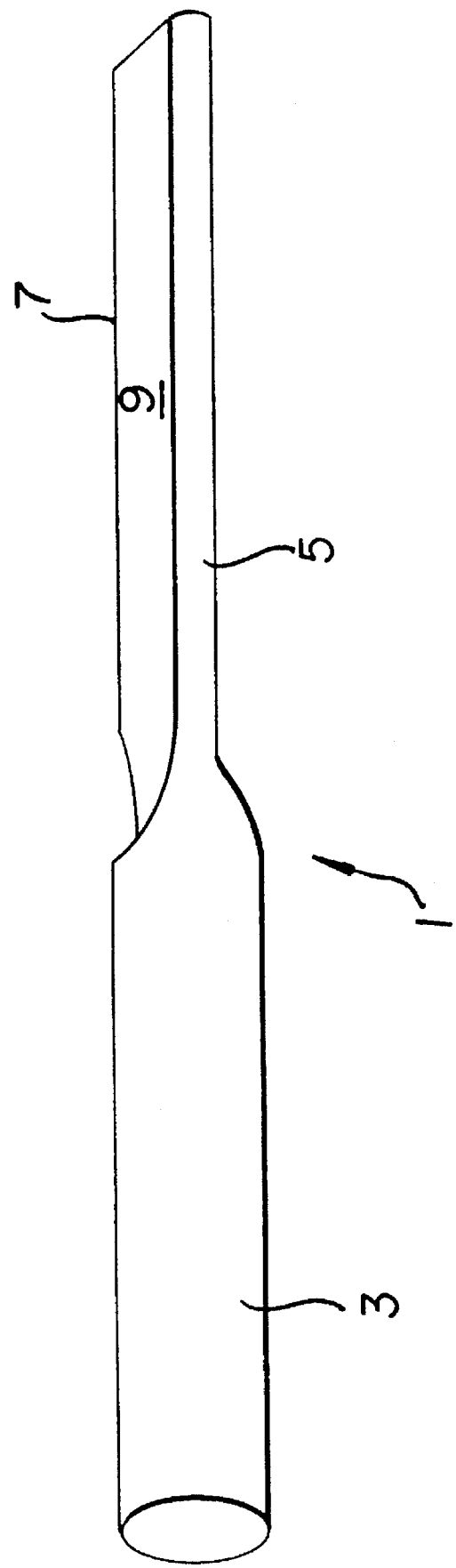

NON-STICK ELECTROCONDUCTIVE AMORPHOUS SILICA COATING

BACKGROUND OF THE INVENTION

This invention relates to electrosurgical instruments, and more particularly to electrosurgical instruments coated with stick resistant electroconductive amorphous silica coating.

In carrying out electrosurgical procedures, an electrosurgical instrument is used which can be energized by a radio frequency voltage source for cutting tissue and/or coagulating blood through cauterization. Such instruments commonly incorporate a conductive blade in either a "monopolar" or "bipolar" system. Although these electrosurgical instruments have proved effective for controlling bleeding during surgery, a common problem associated with the instruments is "tissue-sticking" to the cutting surface and consequently a reduction in cutting efficiency that requires early replacement of the cutting element. One approach to this problem has been to coat the cutting element with some type of non-stick material to which cauterized tissue is less likely to adhere. Of course, such coating material must be suitable for passing electrosurgical current or at least the coating of the material must be arranged to allow passage of current from the cutting surface to the tissue. Illustrative of prior art patents disclosing anti-stick coatings on electrosurgical instruments are U.S. Pat. Nos. 3,754,329, 4,012,551, 4,314,559, 4,222,467, 4,161,950 and 4,481,057.

Although coating electrosurgical instruments with non-stick materials has improved the efficiency of surgical procedures, the coating materials of the prior art still have their shortcomings. For instance, all have been criticized for presenting one or more of the following problems: (1) less than satisfactory electrical conductivity, (2) poor adhesion to the substrate, (3) a tendency to degrade and abrade under the hemostatic and cauterizing currents used during surgery, (4) poor radiation heat transfer reflectivity properties and "outgassing" due to the low melting temperature of the coating material, and (5) reusable surgical instruments undergo surface corrosion and pitting as a result of repeated sterilization cycles. All of these problems result in the cutting surfaces of the electrosurgical instruments becoming coated with charred tissue.

SUMMARY OF THE INVENTION

An object of the invention is to provide an electrosurgical instrument having a new and improved non-stick coating.

Another object of the invention is to provide an electrosurgical instrument having a non-stick coating having excellent conductive properties.

Yet another object of the invention is to provide an electrosurgical instrument having a non-stick coating exhibiting good radiation heat transfer properties.

A further object of the invention is to provide electrosurgical instruments with an anti-stick coating which does not abrade under the cauterizing and hemostatic currents employed during surgery.

Another object of the invention is to provide electrosurgical instruments coated with a coating which poses no "outgassing" problem.

Yet a further object of the invention is to provide reusable electrosurgical instruments with a coating that significantly increases the number of times the tool can be sterilized without imparting significant damage to the surface.

Lastly, an object of the invention is to provide an electrosurgical instrument which exhibits no build-up of charred tissue while surgery is being performed.

These and other objects of the invention are obtained by an electrosurgical cutting instrument comprising a stainless steel body having a cutting edge, said stainless steel body having a non-stick, electroconductive coating of substantially pure amorphous silica deposited on at least the cutting edge by plasma enhanced chemical vapor, said coating being of a thickness that provides electroconductivity when subjected to electrical source generated hemostatic and cauterizing currents during surgery. In an alternative embodiment of the invention, these objects are obtained by an electrosurgical cutting instrument having a cutting edge coated with other inorganic silicon-containing non-stick materials such as molybdenum disilicide or tungsten disilicide which are also applied to a coating thickness that provides electroconductivity during electrosurgery.

The process by which the coated electrosurgical instrument of the invention is obtained involves depositing on at least the cutting edge of the electrosurgical instrument a coating of amorphous silica, said coating being deposited by plasma-enhanced chemical vapor deposition and being of a thickness that provides electroconductivity when subjected to electrosource generated hemostatic and cauterizing currents during surgery.

In a preferred embodiment of the invention, the surface of the electrosurgical instrument is abraded or etched prior to the plasma enhanced chemical vapor deposition.

The plasma enhanced chemical vapor deposition (PECVD) technique employed to coat the electrosurgical instruments of the invention is well known in the art and uses glow discharge to activate the chemical vapor deposition. Instead of requiring thermal energy as in thermal CVD, the energetic electrons in the plasma (at pressures ranging from 1 to 5×10 Pa or 0.01 to 5 torr, typically less than 10 Pa or 0.1 torr) activate almost any chemical reaction among the gasses in the discharge at elevated temperatures, e.g. 40° to 400° C. At the same time, the bulk of the gas and the substrates do not reach high temperatures because of the nonequilibrium nature of the plasma. A weak discharge at a discharge current density on the order of 1 $MAcm^{-2}$ is sufficient to cause a significant enhancement of the overall reaction rate. In plasma enhanced chemical vapor deposition of silicon dioxide, plasma is generated in a reactor by using a d.c., high-frequency rf or microwave power supply. High-frequency rf discharges are most common. Oxygen is passed into the reactor at a regulated flow rate and flows through the plasma where it dissociates and a silicon source, such as tetraethylorthosilicate (TEOS) is simultaneously introduced into the reactor at a controlled rate downstream from the plasma where they react to form amorphous silica that deposits on a heated substrate. PECVD deposition techniques for silica are described in more detail in "Handbook of Tribiology" by B. Bhusan and B. K. Guptay, ISBN 0-07-005249-2, published by McGraw Hill, Inc., 1991.

DESCRIPTION OF THE DRAWING

The above objects, features and advantages of the invention became apparent from a consideration of the following detailed description presented in connection with the accompanying drawing which shows a perspective view of an electrosurgical knife coated with substantially pure amorphous silica.

DESCRIPTION OF THE PREFERRED EMBODIMENT

Referring to the drawing, there is shown an electrosurgical knife to which is applied a radiofrequency signal for purposes of cauterizing or producing hemostasis simultaneously with the cutting of tissue. The electrosurgical knife generally designated 1 is of stainless steel and comprises a shank 3 at a proximal end, which attaches to an electrosurgical pencil (not shown) which supplies power to the knife and enables the surgeon to more readily hold and guide the knife. At its distal end the knife includes a blade 5, sharpened at edge 7. Each flat surface of the blade 9 is provided with a coating of substantially pure amorphous silica ($SiO_2$) deposited thereon by PECVD.

The adhesion of the silica on the stainless steel surface of the electrosurgical instrument can be improved significantly by first pretreating the portion of the blade surface receiving the silica coating so as to improve the interface bond between the PECVD silica layer and the surface of the stainless steel blade being coated. Any of the conventional pretreatment methods known in the art to abrade or etch stainless steel surfaces can be employed as, for instance, by subjecting the blade to "reducing hydrogen ion plasma" or "argon ion plasma" which breaks down chromium oxide and roughens the surface, grit blasting with glass beads, phosphatizing the surface and similar etching or abrasion techniques. The plasma etching technique is preferred in that it introduces submicron scale surface asperities to provide anchorage and increase the interface area. Grit-blasting using 400 or 440 mesh silica beads produces larger surface asperities, on the order of 10–40 micrometers. If desired, these larger surface features can be produced prior to formulation of submicron features by plasma etching to further enhance the non-stick performance.

The etched or abraded knife is then wiped clean and placed into a PECVD reactor provided with a helical resonator discharge source wherein plasma is generated and oxygen gas and a silicon source such as tetraethylorthosilicate (TEOS) is introduced.

Silica deposition is conducted under the following conditions:

| reactor pressure | 10 to 100 mTorr, preferably 20 to 30 mTorr |
| --- | --- |
| TEOS: $O_2$ flow ratio | 0.03 to 2, preferably 0.5 to 1.0 |
| Deposition Temperature | 40 to 300° C., preferably 100 to 160° C. |
| rf power | 60 to 100 W, preferably 75 to 85 W |
| Total gas flow rate | 16 to 24 SCCM, preferably 19 to 21 SCCM |

The specific operating conditions employed in any given case may vary depending principally on the particular substrate and desired thickness but in all circumstances, the conditions selected are those providing a substantially pure silica film. By "substantially pure amorphous silica film" as used in this specification and the appended claims is meant an amorphous silica film comprising at least 90% $SiO_2$, that is, containing less than 10% impurities such as isolated or associated silanol (SiOH), water and ethyoxy ligands of TEOS. Amorphous silica films which contain greater than 25% of these species tend to be porous, less dense and unstable in an ambient environment. High quality substantially pure $SiO_2$ can be obtained when the deposition is reactant transport limited, i.e. at high temperatures and/or low temperatures e.g. 40°, if care is taken to ensure that the TEOS/$O_2$ flow ratio, R is low. When the deposition is reactant transport limited, the surface concentrations of the deposition reaction precursors (—$OC_2H_5$) and intermediate reaction products (SiOH) are low resulting in no or very little incorporation of these species in the growing film.

The PECVD deposition is continued until a film having a thickness that provides electroconductivity is formed. In most cases, this film thickness will fall in the range of about 0.5 to 1.5 micrometers. With this thickness, radiofrequency electrical energy used during electrosurgery will conduct from the stainless steel blade through the $SiO_2$ coating to tissue being cut to cauterize or cause hemostasis. Yet the non-stick characteristics of the $SiO_2$ coating minimize the sticking of charred tissue to the blade. Silica films having a thickness greater than 1.5 micrometers tend not to be electroconductive or to exhibit insufficient electro-conductivity, while films having a thickness less than 0.5 micrometers cannot withstand the cauterizing and hemostatic currents employed during the surgery. Typically, the amorphous silica-coated electrosurgical blades of the invention possess a dielectric constant of 4.0 to 6.5 micrometers (in comparison, PTFE polymeric coatings have a dielectric constant of 2.1 to 2.2) and have a dissipation factor of 0.001 to 0.002. Electrical properties given in Table 1 make the coated product of the invention well-suited for an electrode and therefore, well suited as an electrosurgical cutting instrument.

TABLE 1

| | Dissipation Factor | Dielectric Constant | Dielectric strength, Volts/micro meters | Volume resistivity ohm.cm | Typical coating thickness, micrometer |
| --- | --- | --- | --- | --- | --- |
| Glass Coating ($SiO_2$) | 0.0020 | 4–6 | 30–35 | $10^{14}$ | 0.6 |

In an alternate embodiment of the invention, the electrosurgical cutting instrument is coated with other suitable inorganic silicon-containing non-stick materials such as inorganic disilicides, particularly molybdenum disilicide ($MbSi_2$) and tungsten disilicide ($WSi_2$). The disilicides are used to coat at least the cutting edge of the instrument and are applied at a thickness which is suitable to impart non-stick qualities to the blade surface yet at the same time allow the instrument to stay electroconductive. In general, these coatings will be applied to a thickness of about 0.5 to 1.5 micrometers, and in order to ensure proper adhesion of the coatings to the stainless steel surface, the disilicide coatings should be of sufficient purity, with the disilicides comprising at least about 80% of the coatings, and impurities comprising less than 20% of the coatings. The disilicide coatings may be applied to the electrosurgical instrument of the invention in any conventional manner well known to one of ordinary skill in the art such as by vapor deposition techniques including the PECVD processes discussed above, but it is believed that sputtering processes will more suitable for applying the disilicide coatings of the invention.

The invention will now be described with reference to the following non-limiting examples:

EXAMPLE I

The blade 5 of the stainless steel electrosurgical knife 1 is on the copper stage of a PECVD reactor. The PECVD reactor is a modified six-way stainless steel cross with a 12" long, 2" diameter Pyrex tube attached to the top feedthrough port using an O-ring seal. Plasma is generated and sustained in the reactor tube by using a radio-frequency powered copper coil designed to operate as a helical resonator at 13.56 MHz. Oxygen enters the reactor from the top of the reactor tube and flows through the plasma where it is dissociated and tetraethylorthosilicate, (TEOS), is introduced into the reactor tube downstream from the plasma, through a variable leak valve. Oxygen gas flow rate is regulated by a mass flow controller and the TEOS flow rate is measured from the pressure rise in the chamber while maintaining a constant pump speed. The reactor pressure is measured using a pressure transducer and controlled using an exhaust throttle valve and the gasses are pumped by a 300 l/s turbomolecular pump.

The copper stage in the reactor tube is heated by circulating hot oil to a temperature of 40° C. and amorphous silica deposited onto the blade 5 using the following conditions:

| reactor pressure | 2.5 mTorr |
|---|---|
| TEOS: $O_2$ flow ratio | 0.03 |
| rf power | 80 W |
| Total gas flow rate | 20 SCCM |

Deposition of amorphous silica is continued until a coating 0.6 microns thick over an approximately one inch length is provided. The PECVD deposition process is repeated to coat the opposite surface of the blade.

Infrared spectrum analysis of the coating thus obtained indicates that it is a dense and non-porous film of substantially pure $SiO_2$ that is stable after soaking in water for 15 hours.

The coated electrosurgical blade is found to possess the following properties:
Dielectric strength (1 MHz)=10 kV/mm
Volume resistivity=$10^{14}$ ohm.cm
Dielectric constant=4
Upper continuous use temperature=1100 deg. C.
Thermal conductivity (at 20 deg. C.)=1.2–1.4 W/m/deg. K.
Thermal expansion (20–1000 deg. C.)=0.5–0.75×$10^{-6}$ per deg. C.
Specific heat (at 25 deg. C.)=750 J/Kg/deg. C.)
Tensile Modulus=65–75 GPa
Tensile strength=1–5 MPa The adhesion of the coating was tested by rubbing another stainless steel tool against the coating. No damage was observed on the glossy coating under approximately 10 lbs (45 Newton) of rubbing load.

EXAMPLE II

The silica coated electrosurgical blades of Example I are tested to determine how much of the silica coating is left behind after electrosurgery. The coated blades were used to perform monopolar electrosurgery on samples of beef at the generator power settings of 100 Watts and 40 Watts using an Aspen electrosurgical generator. A single blade was used in both operations. The testing procedure is as follows:

Each blade was used for a total of 30 seconds at a 100 Watt electrosurgical generator power setting. Total number of "cut" cycles was three and the total number of "coag" cycles was two. Each cut or coag cycle was 6 seconds long. The first three cycles (18 seconds total) the blades were used in the "cut" mode, the second two cycles (12 seconds total), in the "coagulation" mode. The blades were allowed to cool for 10 seconds in between each cut or coag cycle.

The blades at 100 watts got very hot during testing and remained slightly discolored after use.

After the electrocautery experiment, the surface of the blades were analyzed to detect the presence of silica, especially near the tip where intense fulguration occurred. Typically, three measurements were taken; very near the tip, the middle of the blade, and the end of the blade (near the shank portion). Silica was detected along the entire length of the blade. The silica level was very low at the tip and linearly increased to its original value over the functional length of the blade. The silica reaches to about 30 percent of its original value over a distance of 10 mm from the tip.

Based on EDX spectra the total silica loss from the blade is estimated to be about 80–100 micrograms after 30 seconds of cut and coag at 100 Watts. The total amount of amorphous silica on the electrosurgical blades is approximately 160 micrograms.

Very little silica loss occurred at 40 watts following the experimental procedure described above. The silica coating remains nearly intact at the generator setting of 40 watts.

EXAMPLE III

Two groups of samples were made by pre-treating the stainless steel substrate with (1) reducing hydrogen ion plasma and (2) argon beam plasma, respectively. Both of these pretreatment procedures create submicron-sized surface asperities which thus physically improve adhesion. In addition, the hydrogen ion plasma treatment chemically enhances interface adhesion. These pre-treated blades were then coated and tested following the identical procedure given in Example II. In each group of samples, the EDX-spectra showed no evidence of coating loss after the test procedure at a power setting of 100 watts.

Although the invention has described with reference to electrosurgical blades, it is not so limited. The invention finds equal applicability to other monopolar and bipolar electrosurgical instruments such as scissors, forceps, scalpels and the like.

It is to be understood, therefore, that the above-described arrangements are only illustrative of the application of the principles of the present invention. Numerous modifications and alternative arrangements may be devised by those skilled in the art without departing from the spirit and scope of the invention.

It is claimed:

1. An electrosurgical cutting instrument comprising a stainless steel body having a cutting edge, said stainless steel body having a non-stick, electroconductive coating of substantially pure amorphous silica deposited on at least the cutting edge by plasma enhanced chemical vapor, said coating being of a thickness that provides electroconductivity when subjected to electrical source generated hemostatic and cauterizing currents during surgery.

2. An electrosurgical cutting instrument according to claim 1 wherein the thickness of said coating is 0.5 to 1.5 micrometers.

3. An electrosurgical cutting instrument according to claim 1 wherein said body is a stainless steel blade.

4. An electrosurgical instrument according to claim 1 wherein the stainless steel body comprises stainless steel surgical scissors.

5. An electrosurgical cutting instrument according to claim 3 wherein the coated blade possesses a dielectric strength ranging from 5 to 50 volts per micrometer.

6. An electrosurgical cutting instrument comprising a stainless steel body having a cutting edge, said stainless steel body having a non-stick, electroconductive coating of an inorganic disilicide deposited on at least the cutting edge of said instrument, said coating being of a thickness that provides electroconductivity when subjected to electrical source generated hemostatic and cauterizing currents during surgery.

7. An electrosurgical cutting instrument according to claim 6 wherein said inorganic disilicide comprises molybdenum disilicide.

8. An electrosurgical cutting instrument according to claim 6 wherein said inorganic disilicide comprises tungsten disilicide.

9. A process for the manufacture of an electrosurgical instrument comprising coating at least the cutting edge of a stainless steel electrosurgical instrument with substantially pure amorphous silica, said coating imparting non-stick characteristics to the cutting edge and being of a thickness that provides electroconductivity when subjected to electrical source generated hemostatic and cauterizing currents during surgery.

10. A process according to claim 9 wherein the thickness of said coating is 0.5 to 1.5 micrometers.

11. A process according to claim 9 wherein said body is a stainless steel blade.

12. A process according to claim 9 wherein the stainless steel body comprises stainless steel surgical scissors.

13. A process according to claim 9 wherein the surface on which said silica is deposited is pretreated to rough and chemically alter the surface so as to increase adhesion thereto of the deposited amorphous silica.

14. A process for the manufacture of an electrosurgical instrument comprising coating at least the cutting edge of a stainless steel electrosurgical instrument with an inorganic disilicide, said coating imparting non-stick characteristics to the cutting edge and being of a thickness that provides electroconductivity when subjected to electrical source generated hemostatic and cauterizing currents during surgery.

15. A process according to claim 14 wherein the inorganic disilicide comprises molybdenum disilicide.

16. A process according to claim 14 wherein the inorganic disilicide comprises tungsten disilicide.

* * * * *

UNITED STATES PATENT AND TRADEMARK OFFICE
CERTIFICATE OF CORRECTION

PATENT NO. : 5,549,604
DATED : August 27, 1996
INVENTOR(S) : Sutcu et al

It is certified that error appears in the above-indentified patent and that said Letters Patent is hereby corrected as shown below:

Title page, item [21] should read as follows:

[21] Appl. No.: 354,072

Signed and Sealed this

Twelfth Day of November, 1996

Attest:

BRUCE LEHMAN

*Attesting Officer*     *Commissioner of Patents and Trademarks*